(12) United States Patent
Sacco et al.

(10) Patent No.: US 7,899,682 B2
(45) Date of Patent: *Mar. 1, 2011

(54) METHOD AND SYSTEM OF RULE-BASED TRIAGE

(75) Inventors: William J. Sacco, Bel Air, MD (US); D. Michael Navin, Bel Air, MD (US)

(73) Assignee: ThinkSharp, Inc., Towson, MD (US)

( * ) Notice: Subject to any disclaimer, the term of this patent is extended or adjusted under 35 U.S.C. 154(b) by 1629 days.

This patent is subject to a terminal disclaimer.

(21) Appl. No.: 10/944,110

(22) Filed: Sep. 16, 2004

(65) Prior Publication Data

US 2005/0177393 A1 Aug. 11, 2005

Related U.S. Application Data

(63) Continuation-in-part of application No. PCT/US03/08881, filed on Mar. 21, 2003, and a continuation-in-part of application No. 10/385,829, filed on Mar. 11, 2003.

(60) Provisional application No. 60/503,530, filed on Sep. 16, 2003, provisional application No. 60/367,527, filed on Mar. 22, 2002, provisional application No. 60/406,225, filed on Aug. 25, 2002.

(51) Int. Cl.
*G06Q 10/00* (2006.01)
*G06Q 50/00* (2006.01)

(52) U.S. Cl. ............... 705/2; 705/3; 705/4; 235/385

(58) Field of Classification Search ............ 705/2, 3, 705/4; 235/385
See application file for complete search history.

(56) References Cited

U.S. PATENT DOCUMENTS

| 5,809,477 A | 9/1998 | Pollack |
| 5,964,065 A | 10/1999 | Migurski et al. ............ 52/64 |
| 6,305,605 B1 | 10/2001 | Goetz et al. ............ 235/385 |

(Continued)

FOREIGN PATENT DOCUMENTS

JP 10-116023 6/1998

(Continued)

OTHER PUBLICATIONS

CERT-Los angeles, Simple Triage and Rapid Treatment; Dec. 4, 2000, http://web.archive.org/web/20001204193200/http://www.cert-la.com/triage/start.htm.*

(Continued)

*Primary Examiner* — Gerald J. O'Connor
*Assistant Examiner* — Hiep Nguyen
(74) *Attorney, Agent, or Firm* — Blank Rome LLP

(57) ABSTRACT

A method and system for ordering treatment or transport of victims of a mass casualty incident, prior to the incident, by establishing simulated casualty severity scores for each of the victims and considering the casualty severity scores and simulated resource availability. The order of treatment is provided on a card, chart, table or graph. Ordering treatment occurs through an analysis of triage simulations using analytical or mathematical programming techniques considering the severity scores, time periods of treatment delay resulting from constrained resources, estimated survival probabilities, and/or deterioration rates applied to the severity scores due to treatment delay. Alternatively, the order of treatment can be determined through data mining, pattern recognition, or greedy algorithm optimization techniques analyzing survival probability estimates associated with the simulated casualty severity scores, and changes to the survival probability estimates due to time periods of treatment delay resulting from constrained resources.

22 Claims, 3 Drawing Sheets

U.S. PATENT DOCUMENTS

| | | | |
|---|---|---|---|
| 6,383,135 B1 | 5/2002 | Chikovani et al. | 600/300 |
| 6,416,480 B1 | 7/2002 | Nenov | 600/557 |
| 6,499,658 B2 * | 12/2002 | Goetz et al. | 235/385 |
| 6,804,656 B1 | 10/2004 | Rosenfeld et al. | |
| 2002/0011518 A1 | 1/2002 | Goetz et al. | 235/385 |
| 2002/0153413 A1 * | 10/2002 | Piatek et al. | 235/375 |
| 2004/0078223 A1 | 4/2004 | Sacco et al. | |

FOREIGN PATENT DOCUMENTS

| | | |
|---|---|---|
| JP | 11-95648 | 9/1999 |

OTHER PUBLICATIONS

Champion et al., A Revision of the Trauma Score, 1989 The Williams & Wilkins Co., vol. 29, No. 5, The Journal of Trauma.*

CERT-LA S.T.A.R.T., "Simple triage and rapid treatment," *CERT-Los Angeles*, Nov. 27, 2002, http://www.cert-lacom, 8 pages.

EMMCO West, "START's the choice in the EMMCO West Region," Nov. 27, 2002, http://www.emmco.org, 2 pages.

Disaster Medical System, "Triage System, Function 7: Coordination of pre-hospital emergency services," Nov. 27, 2002, http://www.mvemsa.com, 4 pages.

Disaster Response: principles of preparation and coordination, "Triage," Apr. 3, 2003, *Chapter 8*, http://216.202.128.19/dr/disaster-Response.nsf, 23 pages.

MS, "Mass casualty incidents and start triage," Nov. 27, 2002, http://www.co.broward.fl.us, Nov. 27, 2002, 14 pages.

Mass Casualty Incident Program, "Initial triage training," sponsored by A.E.M.S., Nov. 27, 2002, http://www.gc.maricopa.edu, 30 pages.

START, "Simple triage and rapid treatment," *Student Manual*, 23 pages.

Streger, M.R., "Prehospital Triage," *J. Emergency Care*, Jun. 1998, http://www.emsmagazine.com, 8 pages.

Champion, Howard R., F.R.C.S., F.A.C.S., "A Revision of the Trauma Score, The Journal of Trauma", 1989, vol. 29, No. 5, pp. 623-629.

Strosberg, Martin A., "Intensive Care Units in the Triage Mode: An Organizational Perspective", Hospital & Health Services Administration; Spring 1991; 36, I: ProQuest Central; 15 pages.

Weiser, Benjamin; Medicine's Reliability Rivaled by Software; The Washington Post (pre-1997 Fulltext), Washington, D.C., Jan. 1, 1992, p. a.08; 4 pages.

* cited by examiner

METHOD AND SYSTEM OF RULE-BASED TRIAGE

CROSS REFERENCE TO RELATED APPLICATIONS

This application claims benefit of U.S. Provisional Application No. 60/503,530, filed Sep. 16, 2003; the contents of which are incorporated herein by reference in its entirety.

This application is a continuation-in-part of U.S. application Ser. No. 10/385,829, filed Mar. 11, 2003; which application claims benefit of U.S. application Ser. No. 60/367,527, filed Mar. 22, 2002; and U.S. application Ser. No. 60/406,225, filed Aug. 25, 2002; the contents of which are incorporated herein by reference in their entirety.

This application is also a continuation-in-part of International Application No. PCT/US03/08881, filed Mar. 21, 2003; which application claims priority to U.S. application Ser. No. 10/385,829, filed Mar. 11, 2003; and U.S. application Ser. No. 60/367,527, filed Mar. 22, 2002; and U.S. application Ser. No. 60/406,225, filed Aug. 25, 2002; the contents of which are incorporated herein by reference in their entirety.

FIELD OF THE INVENTION

The present invention relates generally to multiple and mass casualty triage, and more particularly to a method and system that determines, for multiple casualty incidents, an efficient triage and transport plan that optimizes survivability through use, in certain embodiments, of a simple card, chart, table or graph.

BACKGROUND OF THE INVENTION

A multiple or mass casualty incident can generally be defined as an emergency or disaster where the number of patients or victims exceeds or taxes available resources, or where resource access is restricted or limited or where resources have to be staged. In contrast to routine emergencies, efficiently responding to a mass casualty incident requires triage protocol and procedures for effectively allocating the limited resources.

Triage, from the French verb trier, means to sort, and is the foundation of mass or multiple casualty management. Traditionally, medical attention and transportation to a next level of care is given first to those with the most urgent conditions. While this is appropriate in circumstances when resources are available for the immediate care of all victims, this does not necessary utilize resources most effectively when resources are limited.

The goal in the most widely used methods of mass casualty triage is typically to "do the greatest good for the greatest number". This goal is not very explicit. A more tangible and measurable goal is to maximize the saving of lives. Achieving this explicit goal requires the maximum utilization of transport and treatment resources in consideration of the timing and availability of those resources, the severity of the injuries of the victims, and their deterioration should care and transport to the next level of care be delayed as a result of resource limitations.

Accordingly, triage shall be referred to herein as an organized evaluation of all casualties to prioritize treatment and/or transport of the casualties. Further, triage includes the consideration for the availability and timing of treatment and transport resources.

When casualties are generated in large numbers, as in a mass casualty incident, local medical resources can easily be overwhelmed. The scene is often in chaos, and the response can be disorganized. As such, the efficient use of resources is compromised, with emergency response personnel left to do the best they can. There is no single, standard, or universal method of triage to support these efforts.

The triage method most widely recognized and used is known as "START," which stands for "Simple Triage and Rapid Transport." START, and its many close variations, categorizes patients into four groups: Immediates, Delayed, Ambulatory or Walking, and Expectant, which are differentiated at the scene through color coded tags. Red (Immediate) patients are those categorized as critically injured, those having problems requiring immediate intervention. These victims are given the highest priority for transport and treatment. Yellow (Delayed) patients are injured, requiring some degree of medical attention, but are not expected to die within the first hour if care is delayed. These victims would be transported once all the Reds have been moved from the scene. Delayed patients are not ambulatory, usually requiring a stretcher for transportation. Green (Ambulatory) patients are not critically injured, and can walk and care for themselves. Black (Expectant) patients are deceased, or have such catastrophic injuries that survival is not expected.

START, and its many variations, provides direction for emergency responders at the scene of an incident. START directs that anyone who can walk be tagged Green and collectively moved to a safe place. Next, remaining casualties are moved to a casualty collection area and rapidly assessed. If a casualty is not breathing, an airway is opened manually. If the patient remains apneic, they are tagged Black; if they begin breathing, they are tagged Red. Patients who are breathing and have a respiratory rate above 30 are tagged Red. If respiration is below 30, circulatory status is assessed. If capillary refill takes more than 2 seconds, the patient is tagged Red. If capillary refill takes less than 2 seconds, mental status is assessed. Patients who can follow simple commands, such as handgrips, are tagged Yellow. Patients who cannot follow simple commands are tagged Red. From the casualty collection area, patients are often then moved to a dispatch area, and later transported as resources provide.

Although START is a widely recognized triage system, it has several limitations. First, START does not consider resource availability in its process. Red tagged victims are transported first, for higher level treatment, regardless of the number of victims or the availability of transport and treatment.

Second, START does not differentiate the severity of victim injuries within its categories, and there can be a wide disparity of severity within a START category. Some casualties are categorized Immediate because of a single measure, and some due to multiple measures, yet all are grouped together, even if actual criticality substantially differs. For example, an unconscious victim is immediately classified as a Red. This patient might have only a mild concussion and might regain consciousness without intervention. Another patient might be unconscious, but also has severe respiratory problems and an accelerated heart rate. START makes no differentiation between these two even though the severity is strikingly different.

Third, START does not consider a patient's survival probability in making triage decisions. This leads to less than accurate prioritization, and a less than optimal resulting percent of survivability. For example, a Red tag victim with very little hope of surviving the trip to the hospital might be the first assigned for transport from the scene, possibly wasting valuable resources. Likewise, a Red tagged victim with very high survival probability might be sent first, even though another victim might benefit more from immediate transport.

Fourth, START does not consider the likely deterioration of victims remaining at the scene while other victims receive transport priority. A victim's survival probability is likely to decline if that victim has to wait at the scene, and this deterioration is victim and injury dependant. A serious limitation of START is that "saveable" Red and Yellow tagged victims might be left at the scene deteriorating while higher priority, but more critically injured victims, receive the limited transport and treatment resources.

Finally, START's goal is not measurable, and therefore not attainable. START's goal is to "do the greatest good for the greatest number." This is well intentioned, but is not precise or explicit. An explicit, measurable goal, such as maximizing the saving of lives, lends itself to review and accountability. With the overlay of constraints of transport and treatment resources, achieving this goal becomes a more rigorous process.

SUMMARY OF THE INVENTION

The present invention is a method and system of triage that determines a severity score for each patient quickly and accurately, and provides a treatment prioritization plan that considers and includes all casualties and all available resources to maximize total survivability, in some cases resulting in as many as seven times the survivability of current triage methods. The present invention includes a score-based mathematical algorithm for resource-constrained triage that explicitly maximizes the saving of lives in consideration of victim injury severity, victim survival probabilities, victim deterioration rates, and resource availability.

The present invention provides a prioritization plan that identifies a specific number of casualties, and the severity score of each casualty, for treatment and/or transport in any given period of resource availability. The computer model of the present invention solves instantaneously, even for large-scale casualty incidents, and is dynamic, as the model can be solved and resolved in real time as victims, resources, and conditions change.

In one aspect of the present invention, a method of mass casualty triage establishes a casualty severity score for each of a plurality of victims, then determines an order of treatment for each of the plurality of victims through consideration of the casualty severity score and resource availability. Any of a number of casualty scoring techniques, either known or to be developed, could be employed. For instance, the casualty severity score could include a sum of coded values assigned for each of a victim's respiratory rate, pulse rate, and best motor response. Or, the casualty severity score could include a refinement of categorical scoring method employed in a triage method known as START. Or, the categorical scoring method could be the Revised Trauma Score, Revised Trauma Score II, or variations thereof. Next, determining an order of treatment for each of the plurality of victims could involve mathematical or analytical programming techniques, such as but not limited to dynamic or linear programming formulations. The method could further calculate a number of expected survivors of a respective casualty incident.

In another aspect of the present invention, a triage method establishes a casualty severity score for each of a plurality of casualties, and then determines an order of treatment for each of the plurality of casualties through consideration of resource availability, the casualty severity scores, and casualty severity score deterioration rates resulting from time periods of transport and/or treatment delay. The casualty severity score deterioration rates, or victim deterioration-with-time rates, could be assumed, could be data-based, or could be determined through consideration of factors selected from one or more of an availability of state-of-the-art, or lesser levels of treatment; a cause of a casualty incident; a type of anatomic injury incurred by the victim; an age of the victim; treatment available at the incident scene; treatment available at other facilities; distances to the other facilities; and, facilities or equipment available for performance of casualty management.

In another aspect of the present invention, a triage method first assesses a respiratory rate, pulse rate, and best motor response for each of a plurality of casualties and assigns a coded value for each based on the assessment. A severity score is then established for each of the plurality of casualties by summing the coded values. Based on the total score, a survival probability is assigned to each severity score. Then, mathematical or analytical programming techniques are used to determine an order of treatment for each of the plurality of casualties. A number of expected survivors of a casualty incident can also be determined by the mathematical or analytical programming techniques.

In another aspect of the present invention, when determining the order of treatment and/or calculating the number of expected survivors, the mathematical or analytical programming techniques can consider one or more of the severity scores, the time periods of treatment delay resulting from constrained resources, the survival probabilities, and the deterioration rates applied to the severity scores due to the time periods of treatment delay. Further, the survival probability can be assumed, can be data-based, can be based upon at least one characteristic of a respective casualty or of an incident responsible for the casualty, or can be determined through consideration of one or more of an availability of state-of-the-art, or lesser levels of treatment, a type of anatomic injury incurred by the victim; an age of the victim, treatment available at the incident scene, treatment available at other facilities, distances to the other facilities, and/or facilities or equipment available for performance of casualty management.

In another aspect of the present invention, a card, chart, table or graph is provided that illustrates the results of the triage methods of the present invention summarized above, as directed to simulated casualty incidents. The card provides quick, practical, and suboptimal maximization of survivability without requiring the use of computers or the calculation of algorithms in response to a casualty incident because the ordering is determined prior to the respective casualty incident. In this aspect, the ordering of treatment or transport, for display on the card, chart, table or graph, can be determined by running triage simulations of random or uniformly generated victim distributions and resource constraints, in accordance with the triage methods summarized above. Or, the order of treatment can be determined by employing data mining, pattern recognition, greedy algorithm and/or other exploratory analyses. For example, using a greedy algorithm, determining an order of treatment for each of the plurality of victims can involve determining a change in survival probability for each casualty severity score based upon a consideration of victim deterioration-with-time over an estimated time period to clear the mass casualty incident, and ordering treatment or transport in accordance with an order of maximum change in survival probability. In any event, use of the card, chart, table or graph is directed to optimizing triage, to the greatest degree possible, without requiring ordering determination at the time of the triage event.

BRIEF DESCRIPTION OF THE DRAWINGS

For the purpose of illustrating the invention, there is shown in the drawing one embodiment of the present invention; it being understood, however, that this invention is not limited to the precise arrangements and instrumentalities shown.

DETAILED DESCRIPTION OF THE INVENTION

Figure 1:
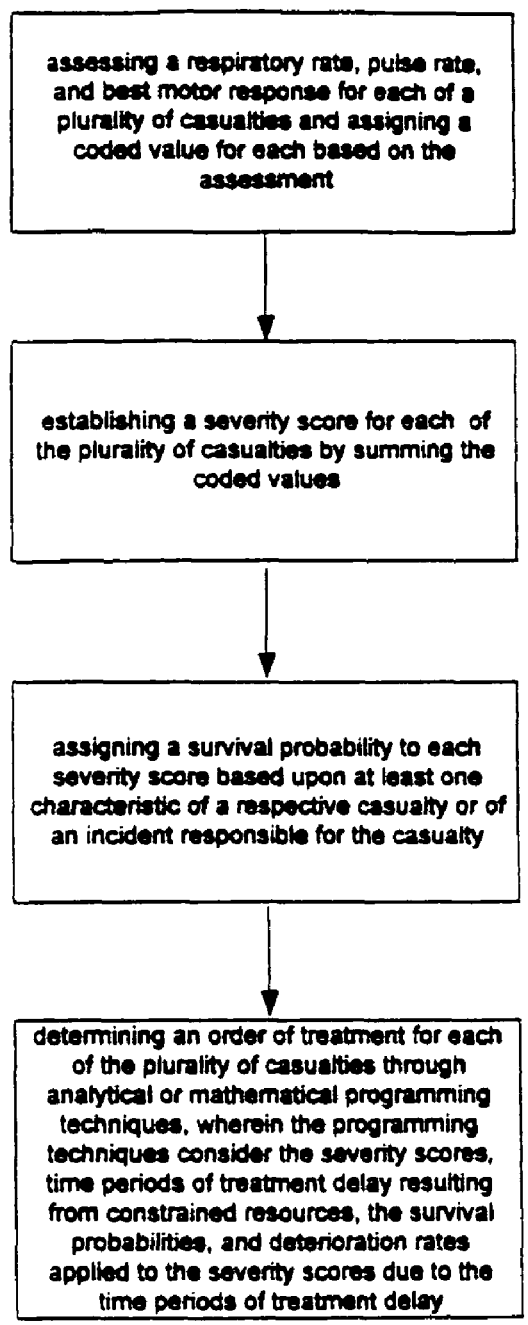
FIG. 1 is a flow diagram illustrating a method of triage in accordance with one embodiment of the present invention.

The present invention provides a method of managing triage for multiple and mass casualty incidents. Generally, the method of the present invention includes the following procedures:

1. Determining a casualty severity score for each victim; and
2. Determining a priority order of treatment for the victims.

The goal of the present invention is to maximize the expected number of survivors in any multiple or mass casualty or resource constrained triage incident. Achieving this goal requires, as resources become available, determining an order upon which victims will be treated, or upon which victims will be transported for treatment, or some combination thereof.

Accordingly, determining a priority order of treatment could occur at the incident scene, and be directed to an order of victim transport to a medical facility. Or, the priority order could be directed to an order of initial treatment at the incident scene, with or without further transport to a medical facility. Or, determining a casualty severity score for each victim, and determining an order of treatment, could occur at an emergency room, or other medical facility intake area, to facilitate optimal triage management at a more specific and localized area remote from an casualty incident scene.

In a catastrophic event, a multiple or mass casualty incident, or any casualty incident where transport and treatment resources are limited, a major issue confronted by triage personnel is that not all of the injured can receive state-of-art treatment instantaneously due to limited resources, either at the incident scene or at further echelons of care, such as holding areas, emergency departments, and resuscitation bays. For the foregoing reasons, the present invention contemplates use in any location, and for any incident, where optimal triage management procedures would result in maximizing victim survival.

For purposes of resolving a triage problem, the present invention recognizes time periods, each time period represented by an amount of resources available for treatment and/or transport of casualties. Due to the likely limitation on resources, certain casualties may wait one or more time periods before receiving treatment by or transport to upper echelons of care. Time periods may be of variable length, and the resources available during any one time period may or may not be equal to the resources available during other time periods. The present invention recognizes the importance of full and efficient utilization of resources across all time periods, and contemplates employment of certain problem solving methods to ensure full and efficient utilization of resources across all time periods. For instance, if time period length is essentially defined by emergency transport time in route to a certain upper echelon care facility, the present invention could employ problem solving techniques such as Dijkstra's method to minimize time in route.

In one aspect of the present invention, the casualty severity scoring method used is "RPM," a method using coded values of a casualty's Respiratory rate, Pulse rate, and best Motor response (a measure of neurological status). It is envisioned that the present invention could employ other methods of casualty scoring, or variations of the RPM model detailed herein, as various scoring applications, either known or to be developed, could easily be adapted to the broad concepts of the present invention. By way of example, the present invention could alternatively incorporate Revised Trauma Score (RTS), the recognized triage standard of the American College of Surgeons. Further, several other abbreviated physiologic severity scores exist and could be incorporated into the present invention, including RPV (based on respiratory rate, pulse rate, and best verbal response), body-region-injury dependent RPV, body-region-injury dependent scores (based on respiratory rate and pulse rate), the Glasgow Coma Scale and best motor response. Also, a scoring methodology could be developed and used based upon the assessment methods currently employed in START.

In another aspect of the present invention, the treatment and triage priorities are then determined from analytical, mathematical, and/or optimization techniques, such as dynamic programming or linear programming, and can incorporate, for greater precision, one or more of data-based estimates of casualty survival probabilities and victim deterioration-with-time rates. The data could be accumulated from previous injury scene data for trauma patients, such as trauma registries, or other mass casualty incidents, or could be estimated based on experts' subjective opinions, with survival probabilities and deterioration rates determined using standard statistical methods.

If incorporating casualty survival probabilities and/or deterioration-with-time rates into the model, a probability or rate could be determined for and used with each of the RPM values. If desired, for greater precision, the survival probability or deterioration rate could be determined using data that considers any one or more of a variety of factors, such as but not limited to an availability of state-of-the-art, or lesser levels of treatment; a cause of or weapon used to create the mass casualty incident (such as a weapon of mass destruction, or a natural disaster); type of anatomic injury incurred by the casualty (such as blunt or penetrating injury, or trauma from blast, chemical, radiological or biological incident); age or age range of the casualty; treatment available at the incident scene, and/or at locations of higher echelons of care; distances to the higher echelons of care; and facilities or equipment available for performance of the casualty management itself. The above list of factors is exemplary, and not limiting, as the casualty survival probabilities and victim deterioration-with-time rates could be a work in progress, continually refined based upon ever-increasing data directed to the above-referenced factors, to other existing factors having available data, or to factors yet to be developed with consideration of the concepts of the present invention.

In another aspect of the present invention, either dynamic or linear programming can be used to determine a priority of treatment for the casualties, each operating irrespective of the specific factors chosen above. The dynamic and linear programming formulations are each directed to maximizing the number of victims saved across all time periods, subject to constraints on available resources in each time period and the number of victims of particular severity score available within each time period. The dynamic and linear programming approaches provide essentially the same optimal result, the difference being approach and method of solution. The present invention also envisions using other methods to determine treatment priorities, including heuristic methods, such as but not limited to search theory based solutions and greedy approaches operating to optimize the number of survivors.

For further precision, the dynamic and/or linear programming formulations could maximize the number of victims saved across all time periods by further considering a type of trauma experienced by the victim, a classification of the victim, and/or a type of care center appropriate for and available to the victim. For instance, specific embodiments could consider, in determining prioritization, that the victim has experienced blunt or penetrating trauma, or blast, chemical, radiological, or biological trauma. Considering the type of trauma experienced, in addition to and in conjunction with the consideration of severity score, could further aid the maximization of victims saved by optimizing the prioritizations determined. A class of the victim could consider age and/or previous health conditions of the victim, and incorporate same into the considerations above. For type of care center, the dynamic or linear programming could determine a priority of treatment based upon a further consideration of matching a type of injury to specific care centers and/or doctors appropriate for and available to the victim, to avoid inefficiencies possible when a victim is transported or received for treatment, but then cannot receive same because needed specialty care is not available at that time, or at that location.

In another aspect, the present invention also includes software to encapsulate the methods expressed herein, the software also providing management assistance for performance of each step of the respective method employed. The software would be compatible with standard personal and laptop computers, and compatible with mobile devices, such as PDAs (i.e. Personal Digital Assistants), presently existing or to be developed, the software providing management assistance and method capability at the incident scene, at one or more remote locations, or at any combination thereof.

In still another aspect of the present invention, triage strategy is determined by software at a central processing location, with coordinated programming by hand held devices located at the incident scene. This aspect employs fully automated dispatch, matching victims with transport and hospital resources through automated data communication. Alternatively, the methods of the present invention could be carried out using a command center approach, where two-way radios communicate necessary data to central control. Further, a simulation driven, rule based protocol could be established having control in the field. In the simulation driven approach, emergency personnel would arrive at a casualty event and quickly characterize the scene and the resources available (i.e., generally characterize a number and a severity of casualties in relation to resource availability, thereby determining a degree of resource constraint). Next, as individual victim assessment begins, the characterization of the entire event is associated with one of several (or more) protocols. The protocol provides direction regarding an order of treatment necessary to maximize total survivability for a given casualty event, and each protocol is pre-established based on simulations including certain assumptions, or facts, about the given casualty event. The quick characterization of the entire event guides the emergency personnel in a selection of a pre-established protocol most closely resembling the casualty incident at issue.

By way of example, the following describes certain aspects of the present invention:

RPM Scoring

RPM is the sum of coded values of respiratory rate (RR), pulse rate (PR), and best motor response (BMR). In one embodiment, the coded values are:

| RR: | 0, | 1-9, | 10-24, | 25-35, | 35+ |
|---|---|---|---|---|---|
| Coded Values | 0 | 1 | 4 | 3 | 2 |
| PR: | 0, | 1-40, | 41-60, | 61-120, | 120+ |
| Coded Values | 0 | 1 | 2 | 4 | 3 |
| BMR: | None, | Ext/Flex, | Withdraws, | Localizes, | Obeys Commands |
| Coded Values | 0 | 1 | 2 | 3 | 4 |

In this embodiment, RPM takes on integer values from zero (0) to twelve (12). RR is measured in breaths/minute, and is implemented by measuring breaths for fifteen (15) seconds and multiplying by four (4). PR is measured in beats/minute, and is implemented by measuring beats for fifteen (15) seconds and multiplying by four (4). BMR assesses the ability of the casualty to respond with movement to stimuli as follows:

Obeys Commands: This requires an ability to comprehend instructions given by verbal command. The casualty must perform the specific movement requested. The following could be a typical routine: the first verbal command is "raise your hand"; if the casualty does so, the assessment is Obeys Commands; if not, the second command is "squeeze my hand"; if the casualty does so, the assessment is Obeys Commands; if not, a painful stimulus, preferably a "nail bed" stimulus, is applied to try to produce a response.

Localizes pain: After painful stimulation, the casualty reaches and/or tries to remove the source of pain.

Withdraws: After painful stimulation, there is flexion of elbow, with rapid movement and no muscle stiffness, and the arm is drawn away from the trunk.

Flexion: After painful stimulation, the elbow flexes slowly accompanied by stiffness, and the forearm and hand remain held against the body.

Extension: After painful stimulation, the legs and arms extend. This movement is accompanied by stiffness and there is internal rotation of the shoulder and forearm.

None: No response to pain.

In one embodiment of the invention, the following is a sample calculation of RPM: If RR=16, PR=50, and BMR is "Obeys Commands", then the coded values are 4, 2, and 4 (from above), and the sum of the coded values (the RPM) equals ten (10).

Casualty Survival Probabilities

By way of example, in one embodiment of the present invention the following are the survival probabilities associated with each RPM value. The survival probabilities presented below are based upon data compiled from various hospital and state-wide trauma statistics involving thousands of casualties.

| RPM Value | Survival Probability |
|---|---|
| 12 | .992 |
| 11 | .985 |
| 10 | .970 |
| 9 | .970 |
| 8 | .910 |
| 7 | .830 |
| 6 | .720 |
| 5 | .570 |
| 4 | .410 |
| 3 | .270 |
| 2 | .160 |
| 1 | .090 |
| 0 | .052 |

Victim Deterioration-with-Time Rates

By way of example, in one embodiment of the present invention the following presents victim deterioration-with-time rates for casualties who remain at the incident scene and continue to receive first respondent treatment at most. The deterioration-with-time rates presented below are based upon interviews with trauma center personnel directed to experiences and statistics of trauma victims and their respective treatment.

| RPM values | Score Point Decrease/30 minutes |
|---|---|
| 11-12 | 1** |
| 8-10 | 1 |
| 5-7 | 2 |
| 3, 4 | 3 |
| 2 | 2 |
| 1 | 1 |
| 0 | 0 |

**For RPM values of 11-12, the score point decrease of one (1) occurs over two (2) thirty (30) minute time periods.

Note:
an example helps to interpret the table. A victim with a first assessment RPM value of eight (8) would have a value of seven (7) thirty (30) minutes after the first assessment, and a value of five (5) one (1) hour after the first assessment with an associated decrease in survival probability from .91 to .57.

Figure 2:
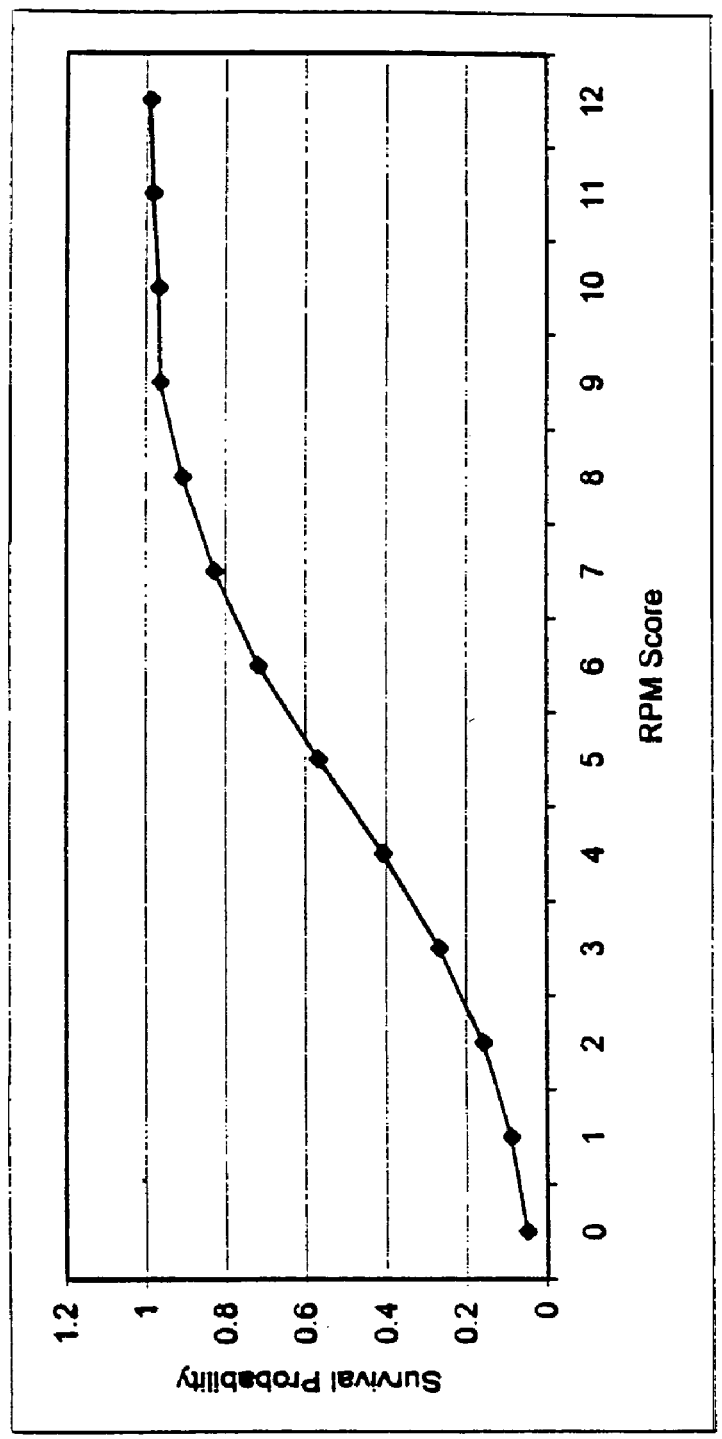
FIG. 2 is a graph illustrating a relationship between survival probability and casualty severity score in accordance with an embodiment of the present invention.

Casualty Survival Probability in Relation to Victim Deterioration-with-Time Rates FIG. 2 illustrates graphically the specific survival probabilities presented above in relattion to respective RPM score. The plotted points of FIG. 2 create an "S"-shaped curve, the "S"-shaped curve including somewhat leveled-off survival probabilities at the high and at the low end of the RPM values, but demonstrating a substantial decrease in, or declining, survival probability between the RPM scores of approximately seven (7) and four (4). Combining this finding with the specific deterioration-with-time rates presented above, it can be seen that, over the entire range of RPM scores, there is a crucial and central range of rapid deterioration in survival probability for RPM scores between 7 and 4).

Determining Treatment and/or Transportation Prioritization

By way of continued example, in one embodiment of the present invention casualty prioritization for treatment and/or transportation is determined by combining: 1) RPM severity scoring and associated survival probability estimates; 2) victim deterioration-with-time rates for those casualties remaining at the incident scene and receiving only first-respondent treatment; and 3) dynamic programming and linear programming.

The RPM value is assessed for each casualty by first responders. The underlying assumption is that the human body responds in specific ways to trauma, depending on the severity of the trauma. More severe trauma results in physiological changes from normal which are greater than those associated with less serious trauma. As with all physiologically based severity scoring, the time interval between the trauma and the assessment can affect the severity score, since the response of body systems to trauma is not instantaneous, but graded over time. There is great value in serial assessments and the charting of changes in the value of assessments over time.

To complete the prioritization process, the dynamic or linear programming problem is solved, the formulation of the problem appearing below:

Stochastic Dynamic Programming Formulation

Let O (N)=Maximum Expected number of Survivors for N casualties in the event where $N=(n_0, n_1, \ldots, n_k)$; $n_i$=the number of victims with a severity score equal to i, where $i=0 \ldots k$. The problem can then be formulated as a multidimensional, stochastic dynamic programming problem as follows:

$$O(N)=\text{maximum [expected survivors (subset triaged first)}+O(N')](STF)$$

where, STF=subset of patients selected for first transport and/or first treatment, and $N'=(n_0', n_1', \ldots, n_k')$.

Notes on the formulation of this embodiment of the present invention:

1. The number of patients in the subset STF will correspond to the number of patients that can be treated by the resources in the next echelon of treatment available.
2. N is a state vector which reflects the numbers of patients not included in the first group triaged and their predicted RPM values at the time of triage for the next group.
3. The mass casualty triage problem is a multistage problem with successive stages being a selection of a subset of patients for triage to the next echelon of care. The quantity inside the brackets [ ] gives the expected number of survivors for an arbitrary selection of the first patient set to be triaged (first term inside the brackets) plus the second term inside the brackets, which is the maximum expected number of survivors "for the remaining stages" given the casualty state (status) of the remaining (nontriaged) casualties at the time of next opportunity to triage. Accordingly, the quantity inside the brackets represents one arbitrarily triaged subset (the first subset triaged) and "optimal" triaging thereafter.

The symbol $$\underset{STF}{\text{---maximum---}}$$

in front of the brackets reflects that the first subset of casualties to be treated or transported will also be optimized, thus making the entire ordering process optimal.

Linear Programming Formulation

The linear programming formulation maximizes the number of victims saved across all time periods, subject to constraints on the amount of medical resources available in each time period, and the number of victims with each severity score. Mathematically, if we let $V_{st}$=victims treated in time period t with severity score s, and $P_s$=the survival probability of treated victims with severity scores s, then the Linear Programming formulation is as follows:

$$\text{MAX} \Sigma_{st} P_s V_{st}$$

subject to $\Sigma_t V_{st}$=number of victims of score s, for all values of s $\Sigma_s V_{st} \leq$ maximum number of victims that can be treated in time period t, for all values of s (this limits the resources).

The linear programming formulation identifies the number of victims with each score and in each time period to be treated such that the overall number of survivors is the maximum possible, given the limitation on available resources. The model of the present invention yields a completely feasible solution, solves very quickly using commercially available linear programming software, and does so even when operating under a large-scale mass casualty situation. The model of the present invention predicts survivability based on the survival probabilities used for each severity score, and is influenced by deteriorations-with-time rates as considered for the waiting victims. This formulation is easily expanded to directly include one or more of a variety of considerations, and/or to indirectly include the one or more variety of considerations through differentiated survival probabilities and/or differentiated deterioration-with-time rates. The variety of considerations could include, but would not be limited to, an availability of state-of-the-art, or lesser levels of treatment; a cause of or weapon used to create the casualty incident; type of trauma incurred by the casualty; a classification of the casualty, such as age or previous health condition; a type of care center appropriate for and available to the casualty, and/or treatment available at the incident scene; distances to the higher echelons of care; and facilities or equipment available for performance of the casualty management itself.

An Exemplary Embodiment of the Present Invention

By way of example, the following illustrates a possible casualty incident, and illustrates how the present invention would prioritize respective casualties for treatment in each time period to optimize total survivors over the entire event. The following embodiment has essentially equal results whether using dynamic or linear programming.

Assumptions:
a) 2600 victims
b) Of the 2600 victims, there are 200 victims in each RPM severity score category (RPM=0 through 12) (13 scores×200=2600)
c) 500 victims can be treated in each period
d) Victims will experience the following severity score deterioration-with-time for each time period:

| RPM value at beginning of time period | Score Point Decrease per time period |
|---|---|
| 8-12 | 1 |
| 5-7 | 2 |
| 3-4 | 3 |
| 2 | 2 |
| 1 | 1 |
| 0 | 0 |

Optimal Triage Protocol in Accordance with Dynamic or Linear Programming:
Time period 1
Treat 200 with score of 5
Treat 200 with score of 6
Treat 100 with score of 7
Time period 2
Treat 100 with original score of 7 (now score of 5)
Treat 200 with original score of 8 (now score of 7)
Treat 200 with original score of 9 (now score of 8)
Time Period 3
Treat 200 with original score of 10 (now score of 8)
Treat 200 with original score of 11 (now score of 9)
Treat 100 with original score of 12 (now score of 10)
Time period 4
Treat 100 with original score of 12 (now score of 9)
Treat any victims still surviving (now score of 0)

Treatment or transportation continues through added time periods until all victims are triaged. The present invention is expected to save 1362 of the 2600 casualties when operating within the assumptions presented above.

Presented below is a continuation of the exemplary embodiment (i.e., 2600 victims, including 200 in each RPM category), illustrating how resource constraints impact survivor results and impact an order of treatment that maximizes survivor results. A comparison of survivor results is also presented between the methodology of the present invention and the worst-first sorting philosophy of START. For instance, in column 2, where 50 victims can be treated in each time period, the methodology of the present invention directs that casualties with an RPM score of 11 are treated in each of the first 4 time periods (50 per period), thereby first accounting for all casualties with an RPM score of 11; then casualties with an RPM score of 12 are treated in each of the next 4 time periods (50 per period), with continued treatment through added time periods as survivors permit. The scenario detailed above, where 500 victims can be treated in each time period, is also shown in table form, below, in column 5.

| Victims in Each RPM Category | 200 | 200 | 200 | 200 | 200 |
|---|---|---|---|---|---|
| Resources in Each Time Period | 50 | 100 | 200 | 500 | 800 |
| Treatment Order (by RPM score per time period) | | | | | |
| $1^{st}$ | 11 | 9 | 7 | 5,6,7 | 4,5,6,7 |
| $2^{nd}$ | 11 | 10 | 8 | 7,8,9 | 8,9,10,11 |
| $3^{rd}$ | 11 | 10 | 9 | 10,11,12 | 12 |
| $4^{th}$ | 11 | 11 | 10 | 12,4,3 | — |
| $5^{th}$ | 12 | 11 | 11 | 2,1,0 | — |
| $6^{th}$ | 12 | 12 | 12 | — | — |
| $7^{th}$ | 12 | 12 | — | — | — |
| $8^{th}$ | 12 | — | — | — | — |
| Max Saves | 1582 | 1582 | 1582 | 1582 | 1582 |
| Present Invention Saves | 434 | 693 | 1068 | 1362 | 1474 |
| Worst First | 135 | 135 | 135 | 720 | 1224 |

Comparison of START and the Present Invention

Recall that START employs severity categorizing based on three observations: respiration, perfusion, and mental status. In START, severity categorization is not specifically delineated, nor is it a computed score. Rather, START provides a method for quickly classifying a victim into one of four categories. Again, the categories are Ambulatory (or Minor), Immediate, Expectant (or Dead), and Delayed.

Ambulatory: All casualties are asked to stand up and walk to a specific area. All that can are designated as ambulatory or minor.

Immediate: A casualty is designated Immediate if breathing with a respiratory rate greater than 30 breaths/minute; OR, pulse is absent for 5 to 10 seconds or is "irregular"; OR, the victim cannot follow the commands "open your eyes", "close your eyes", or "squeeze my hand".

Expectant: A casualty is not breathing and does not start to breath with simple airway maneuvers.

Delayed: Any victim who does not fit into any of the three other categories

START employs the following treatment and/or transportation prioritization strategy: treat all immediates first, then delayeds, then others as opportunity provides. START does not distinguish among the Immediates, or among the Delayeds, with respect to prioritization for transport and upper echelon treatment. Prioritization for treatment and/or transportation is arbitrary among the Immediates, and then among the Delayeds. This can and does result in substantially more deaths than necessary, as demonstrated herein by example:

Immediates, in accordance with START doctrine, can take on the following present invention RPM component values: coded RR values of 2,3, and 0; PR coded values of 1,2,3, and 4; and BMR values of 0,1,2, and 3. Accordingly, START Immediates can take on present invention RPM values between 1 through 10.

Delayeds, in accordance with START doctrine, can take on the following present invention RPM component values; coded RR values of 1,3, and 4; coded PR values of 1,2,3, and 4; and a coded BMR value of 4. Accordingly, START Delayeds can take on present invention RPM values between 6 and 12.

As mentioned, START then makes no further effort to prioritize casualties categorized as Delayeds (other than the general categorization of being a Delayed) for treatment and/or transport, except to categorize them as an Immediate upon a qualifying reassessment.

The method of the present invention, however, distinguishes every casualty by specific severity score, and then rationally prioritizes each, based upon specific score, for treatment and/or transport. The method of the present invention can result in substantially more survivors than START, perhaps as many as seven times the number of survivors.

By way of example (this example is suggestive and not atypical): suppose there are 500 Immediates with present invention RPMs of 1 (survival probability=0.09 with state-of-art treatment); 500 Delayeds with present invention RPMs of 6 (survival probability=0.72 with state-of-art treatment); and 500 casualties can be treated at a time. As prescribed by doctrine, START triages the Immediates first (without taking into account survival probabilities or deterioration-with-time rates to determine priority), and experiences 45 survivors (0.090×500) among the 500 Immediates. START then experiences 205 survivors (0.410×500) one-half hour later upon triaging the 500 Delayeds (a survival probability of 0.410 is used because the 500 Delayeds have deteriorated to a present invention RPM of 4 in the one-half hour). Therefore, START saves 250 casualties.

The doctrine of the present invention directs the sending of the Delayeds first, experiencing 360 survivors (0.720×500), and experiencing (one-half hour later) an additional 26 survivors (0.052×500) from the Immediates, who began with RPM values of 1 and have deteriorated to a present invention RPM of 0. Therefore, the present invention saves 386 casualties.

A Variation of START as an Embodiment of the Present Invention

Based upon the less than optimal severity categorization of casualties in START, and the lack of ordering of treatment to maximize total survivors, the present invention also includes, in one aspect, a refinement of the START methodology to optimize total survivability. In this embodiment, incident victims are first categorized into one of the four START categories (Ambulatory, Immediate, Expectant, and Delayed) as described above, and by the START methodology described above.

Next, for those in the Immediate and Delayed categories, the respiratory, perfusion, and mental status observations are assessed for each victim in relation to an anatomic region of the body incurring injury, and survival probability rates are determined and assigned to each Immediate and Delayed casualty based upon the respiratory, perfusion, and mental status observations in relation to the anatomic region of the body incurring injury. The survival probability rates used can be assumed, can be data-based, or can be specifically compiled from existing trauma data-bases.

Then, each Immediate and Delayed casualty is further partitioned into one or more subcategories based upon the survival probability rate determined and assigned, so that victims grouped together (in the subcategories) have a lesser variation in likelihood of survival. The refinement of the Immediate and Delayed START categories, into subcategories, provides a more precise indicator of casualty severity for each Immediate and Delayed casualty, leading to a determination of an order of treatment providing maximum survivability. From this point, any of the methods of the present invention described above to determine an order of treatment can be employed to prioritize each of the subcategories of Immediate and Delayed casualties. The result is a more effective START triage method, employing several aspects of the present invention, directed to maximizing the number of survivors of a casualty incident.

An Instructional Program Directed to the Present Invention

In another aspect of the present invention, a training method and program is directed to training first responders in the triage methods of the present invention. First responders are defined generally as any participant in a triage operation, or any emergency care personnel involved in a casualty incident. The training methods and program could include case studies providing trainees with a variety of simulated triage experiences, each providing pre-determined trauma scenarios and injury data, such as casualty severity scores and resource availability, to challenge trainees to make triage decisions at the "incident scene", including determinations directed to an order of treatment and/or transportation for each of the incident casualties. For each triage decision made, the trainees could receive scored results based upon their decisions. The results could be in the form of a likely number of survivors resulting from the respective triage decisions.

Trainees (first responders) can initially use their past training and best judgment to direct their decision-making, then the training program could provide hints, leading questions, and/or additional information (i.e., general assistance) to guide and accelerate the learning process. The general assistance efficiently focuses the trainees on important features and method steps of the present invention, by helping the trainees discover flaws in their pre-training approach. The training process of the present invention can provide a dramatic learning experience, as trainees will experience an outcome based on their simulated triage decisions in terms of a number of survivors. Not only will the trainees learn the triage methods of the present invention, but they will fully understand and appreciate its benefits. Repetitive simulated training employing various case studies will hone skills, resulting in trainees experienced in the mechanics of the triage protocols of the present invention, confident in the outcome of the protocols, and prepared to use them correctly in a crisis. Reference materials could be provided, and case studies could be presented through video and animation, and offered, if desired, online.

Further Variations, Development, and Realizations of the Present Invention

As discussed, the present invention can determine survival probabilities based on physiologic scoring of each casualty at the scene, but the chaos of the incident scene dictates that the severity score be practical, meaning that its implementation is quick and straightforward. For at least blunt-injured and penetrating-injured casualties, RPM has proven it can meet these needs. RPM incorporates Respiratory Rate (RR), Pulse Rate (PR), and Best Motor Response (BMR), and has the following attributes:

- analyses indicate that RPM is a good predictor of survival probability
- the transition for emergency responders from START to RPM of the present invention is easily facilitated since it is based on the three assessments currently used (although not scored) in START.

- the method has been successfully tested with Navy Corpsmen and Navy Seals
- the RPM score can be computed in 45 seconds or less, for each casualty A triage tag, similar to existing triage tags, provides a simple mechanism to score and record the RPM values without requiring computations by emergency responders or hospital triage personnel.

Further Correlation of RPM to Survival Probability Estimates

The table below includes logistic function-generated survival probability estimates based on incident scene determined RPM values for 76,460 blunt-injured patients from a Pennsylvania Trauma Outcome Study. Note that this table provides survival probability estimates alternative to those provided previously, the probabilities of the table below being directed specifically to blunt injuries. Similar specific correlations can be developed for other types of trauma, and to age groupings of the victims.

| Scene RPM Value | Survival Probability Estimate for Blunt Injuries |
| --- | --- |
| 12 | .981 |
| 11 | .967 |
| 10 | .943 |
| 9 | .904 |
| 8 | .842 |
| 7 | .750 |
| 6 | .629 |
| 5 | .489 |
| 4 | .351 |
| 3 | .234 |
| 2 | .147 |
| 1 | .089 |
| 0 | .052 |

Notes Regarding START Classifications in Relation to RPM Values

START does not differentiate victim severity within categories, and severities within each category are widely disparate. This is because some casualties qualify for Immediate based on a single measure (e.g. respiratory rate) and others qualify based on two or three measures. Also, there is a large overlap in severity between Immediates and Delayeds.

This is a striking issue, not appreciated by START users. Indeed, as presented earlier, the RPM values for Immediates can vary from 1 to 10, and the RPM values for Delayeds can vary from 6 to 12. With respect to blunt-injury survival probability estimates based on RPM values, Immediates can vary from 0.9 to 0.943, and Delayeds can vary from 0.629 to 0.981. Accordingly, there is a significant (about 31 "point") overlap in survival probability (0.629 to 0.943), yet START protocol proposes triaging all Immediates before any Delayeds, as Immediates are deemed more critical.

If there is a desire by emergency providers to retain START categories, the present invention could rework START protocols so that, as an example, Immediates could be based upon RPM scores of 1-7, and Delayeds could be based upon RPM scores of 8-12. Or, for instance, an Orange category could be added, so that (Reds) Immediates could be based upon scores of 1-5, Oranges could be 6-8, and (Yellows) Delayeds could be based upon RPM scores of 9-12.

Rule-Based Triage as an Embodiment of the Present Invention

The present invention also includes Rule-Based Triage (RBT) methods for use in triage scenarios having no access to computer processors, or where computer processing of transport and treatment order is inconvenient, or when communications between an incident scene and a remote computing location (i.e., when remote computing locations are employed) are disabled, unavailable, or inadequate. The goal of RBT is to provide practical, suboptimal triage by having available, prior to a casualty incident, an order of treatment or transport determined through triage simulation. By practical, we mean that RBT can be presented on a single sheet or card, or perhaps several cards, in graph, table, or spreadsheet form, for immediate use by triage officers upon arrival at an incident scene. By suboptimal, we mean that total survivability may approach, but may not achieve, the mathematical maximum.

Figure 3:
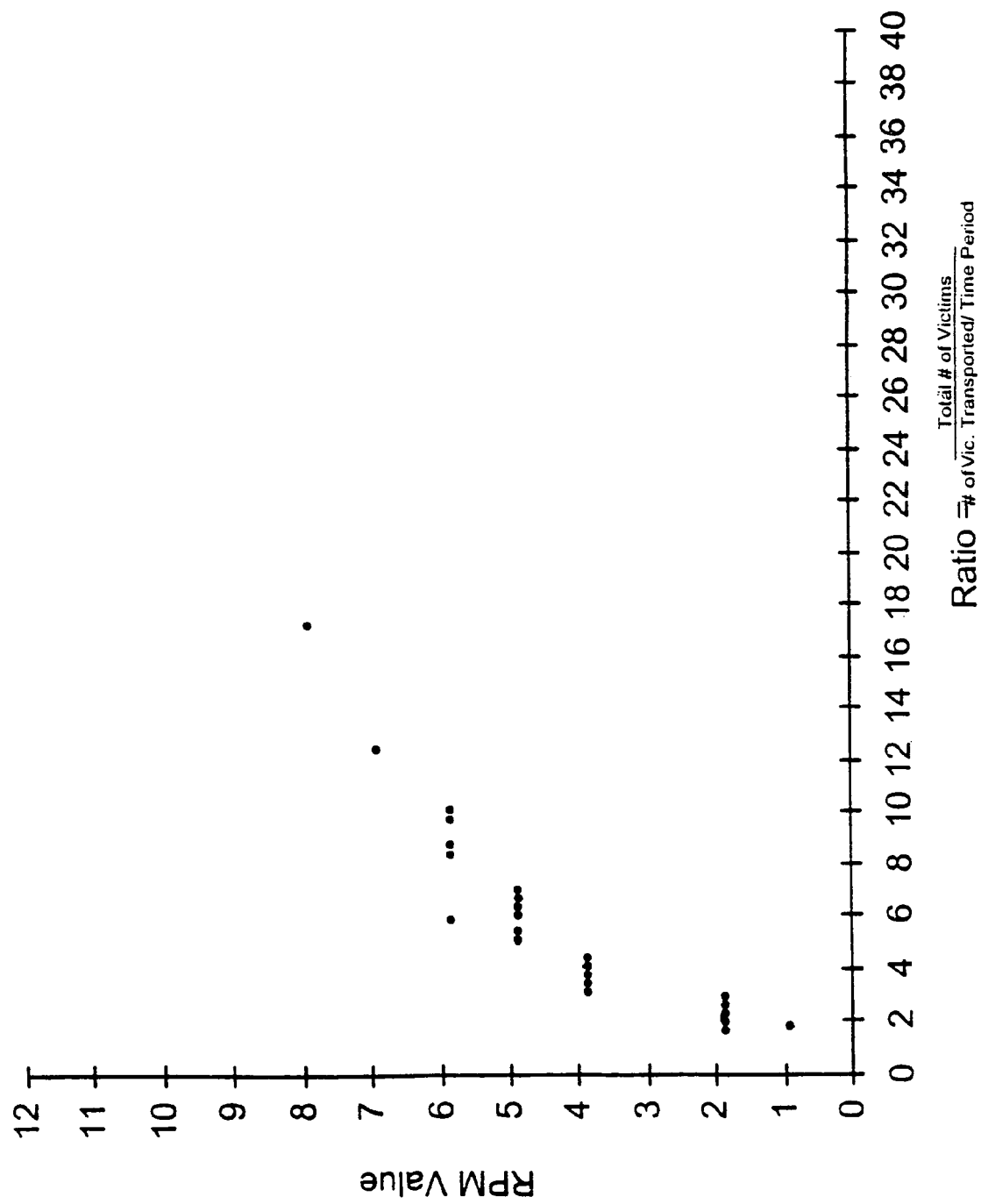
FIG. 3 is a graph illustrating rule-based triage determinations of treatment prioritizations, in accordance with another embodiment of the present invention.

One aspect of RBT is illustrated in FIG. 3, denoted RBT 1, which correlates R (the ratio of the total number of victims/number of victims that can be triaged per time period) to the smallest (lowest) RPM value (sRPMv) selected for triage in period 1. RBT 1 is implemented using a scattergram, with R plotted on the horizontal axis and sRPMv on the vertical axis.

RBT 1 was derived using triage methods of the present invention, determined by running many triage simulations of randomly generated (from various distributions) "victim state vectors" and variable resources (number of victims that can be treated over time period). A victim state vector requires a specification of 13 numbers which are the number of victims associated with each RPM value (from 0 to 12).

The many triage simulations, derived using the programming formulations described above, were gathered and analyzed to provide, in the form of FIG. 3, what a practical and efficient outcome would likely be, using the programming formulations of the present invention, without actually running the formulations at the time of the triage event. Development of RBT 1 can also exploit concepts such as data mining, pattern recognition, and/or other exploratory analyses. More specifically, the triage simulations used to create FIG. 3 assume a uniform distribution of RPM values across the victim population, meaning that every RPM value would be equally represented across all victims at the scene. Alternative representations of FIG. 3 could be prepared for selected non-uniform distributions, and/or specific incident and/or trauma types. Thus, a triage officer, at the incident scene, could quickly assess the scene, and choose the RBT 1 graph most closely representative of the incident, so that the resulting triage determinations using RBT 1 would be the most optimal of the practical results available.

Using the example casualty incident scene provided previously, and reiterated below, the following illustrates how RBT 1 of the present invention would prioritize respective casualties for treatment in each time period to provide practical and nearly optimal total survivability without use of computers at the incident scene, or without algorithmic calculation at the scene.

Assumptions:
a) 2600 victims
b) Of the 2600 victims, there are 200 victims in each RPM severity score category (RPM=0 through 12) (13 scores×200=2600)
c) 500 victims can be treated in each period
d) Victims will experience the following severity score deterioration-with-time for each time period:

In this example, R (the ratio of the total number of victims/number of victims that can be triaged per time period) would be 2600/500=5.2. R=5.2 would correlate, on FIG. 3, with a RPM score of 5. Accordingly, time period 1 (where 500 victims can be treated) would include treatment of 200 victims with a RPM score of 5 (i.e., all of the RPM=5 victims), 200 victims with a RPM score of 6 (i.e., all of the RPM=6 victims), and 100 victims with a RPM score of 7. Triage determinations in subsequent time periods would continue progressing through ever increasing RPM values as each RPM value is exhausted, at the rate of 500 victims per period.

Another aspect of RBT, denoted RBT 2, is illustrated in the RBT 2 table below, and is based on survival probability estimates using blunt-trauma data and deterioration-with-time estimates provided by trauma surgeons. Alternative RBT 2 tables could be developed using survival probability data specific to other types of trauma, and/or evidence based data directed to the deterioration-with-time of RPM score, considering deterioration-with-time generally, or in light of the specific trauma in question.

Using the survival probability data and the trauma surgeon estimates, RBT 2 employs greedy algorithm techniques to provide practical and suboptimal triage, for use where computers are not available (or convenient) to determine optimal programming formulations. Again, techniques other than greedy algorithms could be employed, techniques such as data mining, pattern recognition, and/or other exploratory analyses to formulate prioritization results without employing the computer processing of programming formulations described herein at the time of the triage incident. RBT 2 is distribution independent, meaning that the survivability results provided by the table are not dependent, from a standpoint of optimality, on whether a uniform distribution of the victims across all RPM values occurs.

In the RBT 2 table, below, each time period is listed, followed by a triage order based upon the original RPM score. The original RPM score refers to that score initially established at the incident scene. Again, RBT 2 does incorporate victim deterioration-with-time, but the re-evaluation of the RPM score due to victim deterioration-with-time is not displayed in the table. Rather, the prioritizations listed for every time period, while considering victim deterioration-with-time, refer to the RPM score originally established.

Again using the example casualty incident scene provided above, a triage officer employing RBT 2 at the example incident scene, would triage, in time period 1 (where 500 victims can be treated), 200 victims with a RPM score of 6 (i.e., all of the RPM=6 victims), 200 victims with a RPM score of 5 (i.e., all of the RPM=5 victims), and 100 victims with a RPM score of 7 (thereby completing the 500 victims treated for this time period). Then, in time period 2 (again, where 500 victims can be treated), would triage 200 victims with a RPM score of 8 (i.e., all of the RPM=8 victims), 0 victims with an RPM=6 (as all RPM=6 victims have been treated in time period 1), 200 victims with a RPM score of 9 (i.e., all of the RPM=9 victims), 0 victims with an RPM=5 (as all RPM=5 victims have been treated in time period 1), and 100 victims with a RPM score of 4 (thereby completing the 500 victims treated for this time period).

Another aspect of RBT, denoted RBT 3, is illustrated in the RBT 3 table below, and provides another aspect of ordering of treatment for suboptimal triage where computers are unavailable, or use at the scene is inconvenient, and/or communications to an off-site processing center (if employed) are compromised, non-existent, or undesirable. RBT 3 does not break out the ordering by time period, but instead provides one order of treatment for all time periods based upon the estimated time necessary to completely clear (i.e., assess and transport) all casualties from the incident scene.

In providing one order of treatment for all time periods based upon the estimated time necessary to completely clear the incident scene of victims, RBT 3 provides three incident scene categories, Resources Stressed, Resources Taxed, Resources Overwhelmed, and provides an order of treatment for each. Resources Stressed refers to a multiple casualty incident requiring about one hour to completely clear the scene of victims; Resources Taxed refers to a scene requiring approximately 2 to 3 hours to clear of victims; and Resources Overwhelmed refers to a scene requiring greater than 3 hours to clear of victims. Alternative variations of RBT 3 could provide a greater or lesser number of categories, each category delineating a time range necessary to completely clear the incident scene of victims. The ordering illustrated in RBT 3 is directed to a composite of blunt and penetrating trauma. Alternative embodiments of RBT 3 can be specific to other trauma types, providing a more optimal ordering for an incident primarily involving, in whole or in part, that specific trauma type, or RBT 3 can illustrate a general ordering to address casualty incidents of any trauma type.

RBT 3
Resources Stressed:
  Triage Order: 6 5 4 3 2 7 1 0 8 9 10 11 12
Resources Taxed:
  Triage Order: 5 6 7 8 4 9 3 2 1 10 11 12
Resources Overwhelmed:
  Triage Order: 6 7 8 5 9 10 4 3 2 1 11 12

The ordering reflected in RBT 3, as that reflected in RBT 1 and RBT 2, can be determined by running triage simulations of random victim scenarios (i.e., a various number of victims with various injury types across a random or uniform range of casualty severity score) and resource constraints, the ordering of treatment or transport being determined prior to the respective incident so that a triage officer could implement an order of treatment or transport based upon a previous simulation, or by matching characteristics of various previous simulations to the respective incident scene to select the most adequate simulation result for use. Or, RBT 3 ordering determinations can exploit data mining, pattern recognition and/or greedy algorithms.

In this embodiment of RBT 3, the Resources Stressed portion was determined using a greedy algorithm, considering that there would be some victim staging to await transport to definitive care, and accordingly, experience some deterioration. The Resources Taxed and Resources Overwhelmed portions of RBT 3 rely on various triage simulations.

To determine the Resources Stressed portion of RBT 3 using the greedy algorithm, the following RPM scores, sur-

RBT 2

| Time Period | RPM Triage Order | | | | | | | | | | | | |
|---|---|---|---|---|---|---|---|---|---|---|---|---|---|
| 1 | original RPM value | 6 | 5 | 7 | 4 | 8 | 3 | 9 | 2 | 1 | 10 | 11 | 12 | 0 |
| 2 | original RPM value | 8 | 6 | 9 | 5 | 4 | 3 | 12 | 7 | 10 | 11 | 2 | 1 | 0 |
| 3 | original RPM value | 7 | 8 | 9 | 5 | 4 | 10 | 11 | 6 | 12 | 3 | 2 | 1 | 0 |
| 4 | original RPM value | 6 | 5 | 11 | 12 | 7 | 8 | 9 | 10 | 4 | 3 | 2 | 1 | 0 |
| 5 | original RPM value | 9 | 10 | 6 | 7 | 8 | 11 | 12 | 5 | 4 | 3 | 2 | 1 | 0 |
| 6 | original RPM value | 7 | 8 | 11 | 6 | 9 | 10 | 12 | 5 | 4 | 3 | 2 | 1 | 0 | vival probabilities, and victim deterioration-with-time rates per 30 minutes were used. Considering the expected RPM value after one time period (30 minutes) of deterioration, as reflected in column 3, a change in survival probability is determined, as reflected in column 4. For example, a victim having an original RPM value of 7 would deteriorate to a 6 after one time period; the change in survival probability would therefore be 0.09 (0.83−0.72=0.09). The greedy method then orders victims to minimize the impact of deterioration, by ranking victims by RPM score in decreasing order relative to the expected change in survival probability. As reflected in the table, the greedy algorithm reflects the following order: 6 5 4 3 2 7 1 0 8 9 10 11 12

| Original RPM | Original Survival Probability | Expected RPM After 30 Minutes | Change in Survival Probability | Ranked by Largest Change in RPM |
|---|---|---|---|---|
| 12 | .992 | 12 | 0 | 8* |
| 11 | .985 | 11 | 0 | 8* |
| 10 | .97 | 10 | 0 | 8* |
| 9 | .94 | 9 | 0 | 8* |
| 8 | .90 | 8 | 0 | 8* |
| 7 | .83 | 6 | .09 | 6 |
| 6 | .72 | 4 | .31 | 1 |
| 5 | .57 | 3 | .30 | 2 |
| 4 | .41 | 2 | .25 | 3 |
| 3 | .27 | 1 | .18 | 4 |
| 2 | .16 | 0 | .11 | 5 |
| 1 | .09 | 0 | .038 | 7 |
| 0 | .052 | 0 | 0 | 8* |

*The RPM scores of 0, 8, 9, 10, 11 and 12 were tied with zero expected change in survival probability, and were ordered by increasing RPM values.

These and other advantages of the present invention will be apparent to those skilled in the art from the foregoing specification. Accordingly, it will be recognized by those skilled in the art that changes or modifications may be made to the above-described embodiments without departing from the broad inventive concepts of the invention. It should therefore be understood that this invention is not limited to the particular embodiments described herein, but is intended to include all changes and modifications that are within the scope and spirit of the invention.

What is claimed is:

1. A method of triage for determining an order of treatment, or transport for treatment, for victims of a mass casualty incident, to maximize the number of survivors of the mass casualty incident, the method comprising the steps of:
   receiving a casualty severity score for each of a plurality of victims of a simulated mass casualty incident;
   inputting each casualty severity score into a computer;
   receiving simulated information indicative of medical transport and trauma center resources available for the plurality of victims;
   inputting the information indicative of medical transport and trauma center resources available into a computer;
   determining by a computer implemented decision logic an order of treatment, or transport for treatment, for each of the plurality of victims, wherein the decision logic mathematically factors the casualty severity scores and the information indicative of medical transport and trauma center resources available for the plurality of victims; and
   distributing the order of treatment, or transport for treatment, to incident personnel, on a rule-based card, chart or graph for use by the incident personnel upon occurrence of a mass casualty incident.

2. The method of claim 1, wherein determining an order of treatment, or transport for treatment, employs a greedy algorithm optimization technique.

3. The method of claim 1, wherein determining an order of treatment, or transport for treatment, involves data mining techniques.

4. The method of claim 1, wherein the graph includes a ratio of a total number of victims over a number of victims that can be triaged per time period on one axis and a range of casualty severity scores on the other axis.

5. The method of claim 4, wherein the graph is used by locating on the one axis the ratio of the total number of victims at the scene over the number of victims that can be triaged per time period and correlating this ratio on the on the other axis with the associated casualty severity score, whereby the associated casualty severity score represents a lowest casualty severity score selected for treatment or transport in time period one.

6. The method of claim 1, wherein the order of treatment, or transport for treatment, provided on the rule-based card is developed by analyzing triage simulations processed using analytical or mathematical programming techniques considering data-based estimates of casualty survival probability and victim deterioration-with-time rates.

7. The method of claim 6, wherein the casualty survival probability is determined through consideration of factors selected from the group consisting of an availability of state-of-the-art, or lesser levels of, treatment; a cause of a casualty incident; a type of anatomic injury incurred by the victim; an age of the victim; treatment available at the incident scene; treatment available at other facilities; distances to the other facilities; and, facilities or equipment available for performance of casualty management.

8. The method of claim 6, wherein the victim deterioration-with-time rates are determined through consideration of factors selected from the group consisting of an availability of state-of-the-art, or lesser levels of, treatment; a cause of a casualty incident; a type of anatomic injury incurred by the victim; an age of the victim; treatment available at the incident scene; treatment available at other facilities; distances to the other facilities; and, facilities or equipment available for performance of casualty management.

9. The method of claim 1, wherein determining an order of treatment, or transport for treatment, for each of the plurality of victims involves running triage simulations of randomly generated (from various distributions) "victim state vectors" and variable resources (number of victims that can be treated over time period).

10. The method of claim 1, wherein the card, chart or graph displays an order of treatment, or transport for treatment, listing casualty severity scores, and determining an order of treatment, or transport for treatment, for each of the plurality of victims involves employing data mining, greedy algorithm, or pattern recognition techniques.

11. The method of claim 1, wherein the card, chart or graph displays an order of treatment, or transport for treatment, listing casualty severity scores, and determining an order of treatment, or transport for treatment, for each of the plurality of victims involves analyses of evidence based data of survival probability and deterioration-with-time estimates.

12. The method of claim 1, wherein determining an order of treatment, or transport for treatment, for each of the plurality of victims involves determining a change in survival probability for each casualty severity score based upon a consideration of victim deterioration-with-time over an estimated time period to clear the mass casualty incident, and ordering treatment, or transport for treatment, by maximum change in survival probability.

13. The method of claim 1, wherein the use by the incident personnel upon the occurrence of a mass casualty incident comprises the steps of:
    characterizing the mass casualty incident by estimating a number and severity of victims at the mass casualty incident in relation to actual medical transport and trauma center resources available, thereby determining a degree of resource constraint at the mass casualty incident;
    associating the characterization of the mass casualty incident to one of prior protocols determined, wherein the prior protocols involve a prior determination by a computer implemented decision logic of an order of treatment, or transport for treatment, for each of the plurality of victims, factoring various ranges of simulated victim numbers, various ranges of simulated casualty severity scores, and various ranges of simulated medical transport and trauma center resources available; and
    selecting the prior protocol most closely resembling the characterization of the mass casualty incident, for use by the incident personnel to direct triage at the mass casualty incident.

14. The method of claim 1, wherein determining by a computer implemented decision logic an order of treatment, or transport for treatment, for each of the plurality of victims, additionally factors one or more of a cause of a casualty incident; a type of injury incurred by the victim; an age of the victim; treatment available at the incident scene; treatment available at other facilities; distances to the other facilities; and, facilities or equipment available for performance of casualty management, and additionally determines a specific care center for one or more of the plurality of victims.

15. A method of triage for determining an order of treatment, or transport for treatment, for victims of a mass casualty incident, to maximize the number of survivors of the mass casualty incident, the method comprising the steps of:
    receiving a casualty severity score for each of a plurality of victims of a simulated mass casualty incident;
    inputting each casualty severity score into a computer;
    receiving simulated information indicative of medical transport and trauma center resources available for the plurality of victims;
    inputting the information indicative of medical transport and trauma center resources available into a computer;
    assigning a plurality of time periods, each time period of length certain;
    inputting the length of time period into a computer;
    determining by a computer implemented decision logic an order of treatment, or transport for treatment, for each of the plurality of victims for each time period, wherein the decision logic mathematically factors the casualty severity scores and the information indicative of medical transport and trauma center resources available for the plurality of victims; and
    distributing the order of treatment, or transport for treatment, or each time period, to incident personnel, on a rule-based card, chart or graph for use by the incident personnel upon occurrence of a mass casualty incident.

16. The method of claim 15, wherein the order of treatment, or transport for treatment, for each time period includes a subset of the plurality of victims to treat or transport during each time period, and identifies a casualty severity score to associate with each of the victims of the subset, whereby a total number of survivors are maximized over all time periods.

17. The method of claim 15, wherein determining an order of treatment, or transport for treatment, for each of the plurality of victims involves determining a change in survival probability for each casualty severity score based upon a consideration of victim deterioration-with-time over the time periods necessary to clear the mass casualty incident, and ordering treatment, or transport for treatment, by maximum change in survival probability.

18. A method of triage for determining an order of treatment, or transport for treatment, for victims of a mass casualty incident, to maximize the number of survivors of the mass casualty incident, the method comprising the steps of:
    receiving a casualty severity score for each of a plurality of victims of a simulated mass casualty incident;
    inputting each casualty severity score into a computer;
    assigning a survival probability to each casualty severity score based upon at least one characteristic of the respective victim or of an incident responsible for the victim;
    inputting the survival probability for each casualty severity score into a computer;
    receiving simulated information indicative of medical transport and trauma center resources available for the plurality of victims;
    inputting the information indicative of medical transport and trauma center resources available into a computer;
    assigning a plurality of time periods, each time period of length certain;
    inputting the length of time period into a computer;
    determining by a computer implemented decision logic an order of treatment, or transport for treatment, for each of the plurality of victims for each time period, wherein the decision logic mathematically factors the casualty severity scores, the information indicative of medical transport and trauma center resources available for the plurality of victims, time periods of treatment delay resulting from constrained resources available for the plurality of victims, the survival probabilities, and deterioration rates applied to the casualty severity scores due to time periods of treatment delay; and
    distributing the order of treatment, or transport for treatment, for each time period, to incident personnel, on a rule-based card, chart or graph for use by the incident personnel upon occurrence of a mass casualty incident.

19. The method of claim 18, wherein the order of treatment, or transport for treatment, for each time period includes a subset of the plurality of victims to treat or transport during each time period, and identifies a casualty severity score to associate with each of the victims of the subset, whereby a total number of survivors are maximized over all time periods.

20. The method of claim 18, wherein the deterioration rates are determined through consideration of factors selected from the group consisting of an availability of state-of-the-art, or lesser levels of, treatment; a cause of a casualty incident; a type of anatomic injury incurred by the victim; an age of the victim; treatment available at the incident scene; treatment available at other facilities; distances to the other facilities; and, facilities or equipment available for performance of casualty management.

21. A method of triage for determining an order of treatment, or transport for treatment, for victims of a mass casualty incident, to maximize the number of survivors of the mass casualty incident, the method comprising the steps of:
    receiving a casualty severity score for each of a plurality of victims of a simulated mass casualty incident;
    inputting each casualty severity score into a computer;

receiving simulated information indicative of triage resources available for the plurality of victims;

inputting the information indicative of the triage resources available into a computer;

determining by a computer implemented decision logic an order of treatment, or transport for treatment, for each of the plurality of victims, wherein the decision logic mathematically factors the casualty severity scores and the triage resources available for the plurality of victims; and distributing the order of treatment, or transport for treatment, to incident personnel, on a rule-based card, chart or graph for use by the incident personnel upon occurrence of a mass casualty incident, wherein upon occurrence of an actual mass casualty incident, use by the incident personnel comprises the steps of:

characterizing the mass casualty incident by estimating a number and severity of victims at the mass casualty incident in relation to actual triage resources available, thereby determining a degree of resource constraint at the mass casualty incident;

associating the characterization of the mass casualty incident to one of prior protocols determined, wherein the prior protocols involve a prior determination by a computer implemented decision logic of an order of treatment, or transport for treatment, for each of the plurality of victims, factoring various ranges of simulated victim numbers, various ranges of simulated casualty severity scores, and various ranges of simulated triage resources available; and selecting the prior protocol most closely resembling the characterization of the mass casualty incident, for use by the incident personnel to direct triage at the actual mass casualty incident.

22. A method of triage for determining an order of treatment, or transport for treatment, for victims of a mass casualty incident, to maximize the number of survivors of the mass casualty incident, the method comprising the steps of:

receiving a casualty severity score for each of a plurality of victims of a simulated mass casualty incident;

inputting each casualty severity score into a computer;

receiving simulated information indicative of triage resources available for the plurality of victims;

inputting the information indicative of the triage resources available into a computer;

determining by a computer implemented decision logic an order of treatment, or transport for treatment, for each of the plurality of victims, including determining a specific care center for one or more of the plurality of victims; wherein the decision logic mathematically factors the casualty severity scores, the triage resources available for the plurality of victims, and one or more of a cause of a casualty incident, a type of injury incurred by the victim, an age of the victim, treatment available at the incident scene, treatment available at other facilities, distances to the other facilities, and, facilities or equipment available for performance of casualty management; and distributing the order of treatment, or transport for treatment, and the specific care center for one or more of the plurality of victims, to incident personnel, on a rule-based card, chart or graph for use by the incident personnel upon occurrence of a mass casualty incident.

* * * * *